US011312793B2

(12) United States Patent
Masere

(10) Patent No.: US 11,312,793 B2
(45) Date of Patent: Apr. 26, 2022

(54) AMINO-QUINONE ANTIPOLYMERANTS AND METHODS OF USING

(71) Applicant: Ecolab USA Inc., St. Paul, MN (US)

(72) Inventor: Jonathan Masere, Richmond, TX (US)

(73) Assignee: Ecolab USA Inc., St. Paul, MN (US)

( * ) Notice: Subject to any disclaimer, the term of this patent is extended or adjusted under 35 U.S.C. 154(b) by 147 days.

(21) Appl. No.: 16/580,653

(22) Filed: Sep. 24, 2019

(65) Prior Publication Data

US 2020/0102408 A1 Apr. 2, 2020

Related U.S. Application Data

(60) Provisional application No. 62/738,342, filed on Sep. 28, 2018.

(51) Int. Cl.
| | |
|---|---|
| C08F 2/40 | (2006.01) |
| C08F 12/08 | (2006.01) |
| C08K 5/08 | (2006.01) |
| C08K 5/17 | (2006.01) |

(52) U.S. Cl.
CPC ............... *C08F 2/40* (2013.01); *C08F 12/08* (2013.01); *C08K 5/08* (2013.01); *C08K 5/17* (2013.01)

(58) Field of Classification Search
CPC ... C08F 2/40; C08F 12/08; C08K 5/17; C08K 5/08
USPC ........................................................ 524/186
See application file for complete search history.

(56) References Cited

U.S. PATENT DOCUMENTS

| | | | |
|---|---|---|---|
| 2,886,494 A | 5/1959 | Anspon | |
| 3,114,755 A | 12/1963 | Covey | |
| 3,179,661 A | 4/1965 | Blumenkopf et al. | |
| 3,193,574 A | 7/1965 | Katchalsky et al. | |
| 3,340,160 A | 9/1967 | Waldby | |
| 3,379,739 A | 4/1968 | Mecke | |
| 3,682,980 A | 8/1972 | Braid et al. | |
| 3,919,265 A | 11/1975 | Bugaut et al. | |
| 3,935,246 A | 1/1976 | Bernauer et al. | |
| 4,023,926 A | 5/1977 | Bugaut | |
| 4,292,047 A | 9/1981 | Vartanian et al. | |
| 4,970,278 A | 11/1990 | Komabashiri et al. | |
| 5,059,662 A | 10/1991 | Wikelski et al. | |
| 5,378,773 A | 1/1995 | Shimizu et al. | |
| 5,420,214 A | 5/1995 | Shimizu et al. | |
| 5,424,003 A | 6/1995 | Shimizu et al. | |
| 5,442,002 A * | 8/1995 | Shimizu .................. | C08F 2/004 524/81 |
| 5,576,274 A | 11/1996 | Patil | |
| 5,583,247 A | 12/1996 | Nesvadba et al. | |
| 5,616,774 A | 4/1997 | Evans et al. | |
| 5,665,126 A | 9/1997 | Patil et al. | |
| 6,024,894 A | 2/2000 | Arhancet | |
| 7,045,647 B2 | 5/2006 | Benage | |
| 9,422,231 B2 | 8/2016 | Bakare et al. | |
| 2002/0037958 A1 | 3/2002 | Benage et al. | |
| 2002/0128499 A1 | 9/2002 | Maender et al. | |
| 2004/0034247 A1 | 2/2004 | Eidin | |
| 2012/0316369 A1 | 12/2012 | Masere | |
| 2014/0200375 A1 | 7/2014 | Subramaniyam | |
| 2016/0304417 A1 | 10/2016 | Masere et al. | |

FOREIGN PATENT DOCUMENTS

| | | | |
|---|---|---|---|
| CN | 102199100 A | | 9/2011 |
| FR | 1289071 | | 3/1962 |
| JP | 2003055288 A | * | 2/2003 |

OTHER PUBLICATIONS

Velikov et al., Journal of Thermal Analysis and Calorimetry, 56, 473-486, 1999. (Year: 1999).*
Trubnikov et al., Polymer Science U.S.S.R., 25, 10, 2497-2504, 1983. (Year: 1983).*
Translation of JP 2003-055288 (patent application 2002-165030), Feb. 26, 2003. (Year: 2003).*
Trubnikov et al. (1983) "Mechanism of the inhibition of polymerization of vinyl monomers initiated by benzoyl peroxide by stable nitroxide radicals", Polymer Science U.S.S.R., 25(10):2497-2504.
Li (2000) "Inhibition effect of methyl methacrylate polymerization by tetramethoxylbenzoquinone-amine charge transfer complexes", Journal of Tsinghua University, 40(2):24-28.
Mereyala et al. (2007) "An Efficient Synthesis of 2,5-Diamino-1,4-benzoquinone", Synthesis, 2:187-189.
Shushunova et al. (2009) "Inhibition of Polymerization of Methyl Methacrylate by an ortho-Benzoquinone-Amine System", Polymer Science (Series B), 51(11-12):427-437.
Saeed et al. (2009) "Synthesis of some 2,5-diamino-3,6-dibromo-1,4-benzoquinones", African Journal of Pure and Applied Chemistry, 3(12):275-280.
You et al. (2012) "Synthesis, biological evaluation, and molecular docking studies of 2,5-substituted-1,4-benzoquinone as novel urease inhibitors", Bioorganic & Medicinal Chemistry, 20(16):4889-4894.
MacGregor et al. (2014) "Development of quinone analogues as dynamin GTPase inhibitors", European Journal of Medicinal Chemistry, 85(6):191-206.
Sieveking et al. (2014) "2-Phenylaminonaphthoquinones and related compounds: Synthesis, trypanoddal and cytotoxic activities", Bioorganic of Medicinal Chemisuy, 22:4609-4620.
Velikov et al. (1999) "Inhibited Oxidation of Cumene and Polymerization of Styrene Investigated by Solution Microcalorimetry", Journal of Thermal Analysis and Calorimetry, 57:473-486.
Gornostaev et al. (2017) "Isomerization of 4-arylamino-1,2-naphthoquinones to 2-arylamino-1,4-naphthoquines", Russian Chemical Bulletin, 66(6):1007-1010.

* cited by examiner

Primary Examiner — Hui H Chin
(74) Attorney, Agent, or Firm — Kagan Binder, PLLC

(57) ABSTRACT

Described are methods and composition for inhibiting polymerization of a monomer (e.g., styrene) composition using an aminated quinone antipolymerant, such as an aminated benzoquinone or aminated naphthoquinone antipolymerant having one or more secondary or tertiary amine group(s). The aminated quinone antipolymerant can be used with little or no nitroxyl group containing antipolymerant yet still provide excellent antipolymerant activity in a monomer-containing composition.

17 Claims, 1 Drawing Sheet

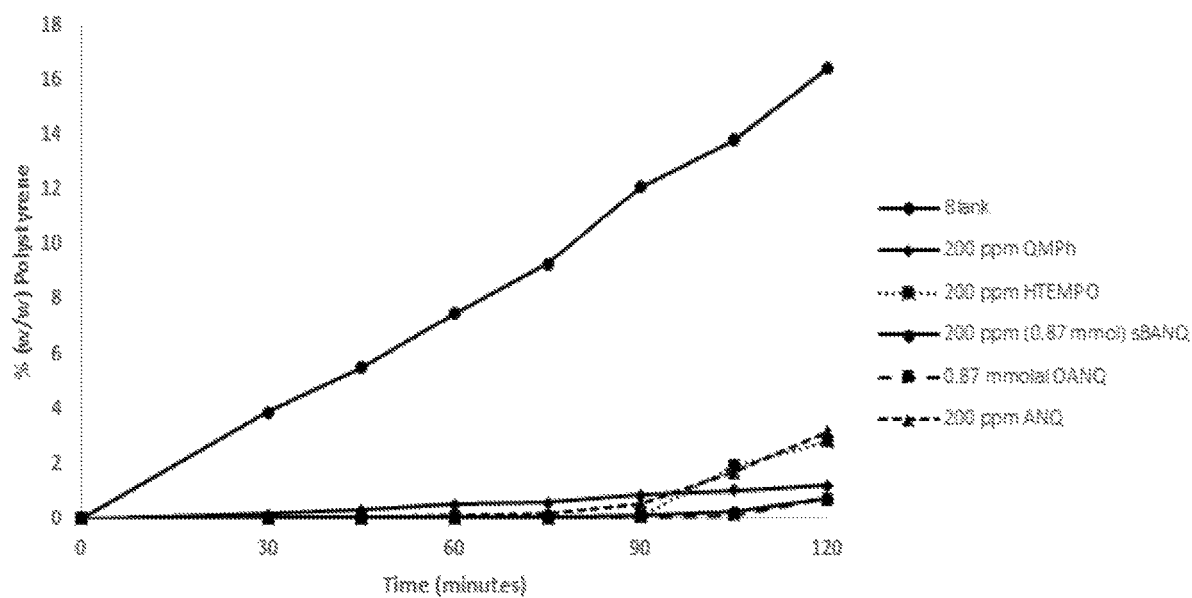

AMINO-QUINONE ANTIPOLYMERANTS AND METHODS OF USING

CROSS REFERENCE TO RELATED APPLICATION

This application claims the benefit of U.S. Provisional Patent Application Ser. No. 62/738,342, filed Sep. 28, 2018, the disclosure of which is incorporated by reference herein in its entirety.

TECHNICAL FIELD

The invention is directed to compositions and use of an aminated quinone antipolymerant compound for preventing premature polymerization of monomers.

BACKGROUND

The high-temperature processing of hydrocarbon stream laden with ethylenically unsaturated monomers like styrene, isoprene, butadiene, for instance can be very challenging. In various chemical industrial processes, the use of high temperatures to purify said monomers can lead to unwanted and problematic polymers. These vinylic monomers undesirably polymerize through radical polymerization especially at elevated temperatures. Similarly, transportation and storage of hydrocarbon streams containing vinylic species can lead to premature polymerization unless antipolymerants are added to said streams. The polymer thus formed can precipitate from solution to foul the process equipment. Removing the foulants becomes necessary. The physical removal or cleaning of the fouled equipment is often expensive. These undesirable polymerization reactions also result in a loss in the production efficiency and the consumption of valuable products. Undesired polymerization reactions are particularly problematic in compositions having vinyl aromatic monomers To prevent undesired polymerization reactions, free-radical polymerization antipolymerants are often added to process streams or stored compositions. However, these compounds are generally consumed quite rapidly. For example, in cases of emergency due to a mechanical or processing problems and where more inhibitor cannot be added, previously added inhibitor will be rapidly consumed. Subsequently, unwanted polymerization reactions will then rapidly recur.

Examples of polymerization inhibitors known in the art include dialkylhydroxylamines, such as hydroxypropylhydroxylamine (HPHA), and stable nitroxide free radicals. Other inhibitors include N,N'-dialkylphenylenediamines, N,N'-diarylphenylenediamines and N-aryl-N'-alkylphenylene-diamines. Quinone diimide compounds are also another class of inhibitors. However, nitroxide-containing compounds can release $NO_x$, making their use undesirable in some situations.

Other types of antipolymerant compounds often referred to as "retarders" slow down the rate of polymerization reactions. However, they are often not as effective as polymerization inhibitors, particularly stable nitroxide free radicals. Polymerization retarders, however, are usually not consumed as quickly as polymerization inhibitors so they tend to be more useful in cases of emergency shutdowns.

Retarders such as sulfur and dinitrophenol (DNP) compounds exemplified by 2,6-dinitrophenol, 2,4-dinitrocresol, and 2-sec-butyl-4,6-dinitrophenol (DNBP), were initially used. However DNP and sulfur retarders release $NO_x$ and $SO_x$ emissions, making their use problematic. Furthermore, DNP-based retarders are highly toxic such that the safety of personnel handling DNP-based antipolymerants is a major concern.

One class of compounds designed to function as a safer substitute for DNP retarders is based on quinone methide chemistry. Quinone methides slow the rate of polymer formation under static conditions and do not need to be frequently re-fed into the process stream. Some quinone methide compounds, however, do not exhibit good stability. Examples of quinone methide compounds are in U.S. Pat. Nos. 4,003,800, 5,583,247, and 7,045,647. The production of styrene typically involves the use of both an inhibitor (e.g., a nitroxide-containing inhibitor such as TEMPO) and a retarder (e.g., a quinone methide). While it is desired in various styrene production situations to eliminate the nitroxide-containing inhibitor, the use of only a retarder has been found to provide insufficient polymerization inhibition, making it difficult to eliminate or minimize inhibitor use.

Technical challenges remain in this area of technology relating to efficacy of compounds used to inhibit or slow polymerization reactions, as well as stability and safety concerns. In spite of the concerns over toxicity, DNP-based antipolymerants remain the most efficient retarders available. Out of safety concerns, there is a need for antipolymerants that are at least as efficacious as DNP-type retarders, but non-toxic.

SUMMARY

The current disclosure is directed to compositions and methods that include or utilize an aminated quinone antipolymerant to inhibit the polymerization of ethylenically unsaturated monomers like styrene and butadiene in various processes and situations, such as purification, fractionation, separation, compression, transportation, and storage of various monomer-containing compositions. Advantageously, the aminated quinone antipolymerant can be used without, or with very little, nitroxyl group-based antipolymerant, yet it still provides excellent ability to inhibit polymerization of monomers in solution.

The use of the inventive aminated quinone antipolymerant compositions mitigates the fouling of process, transportation and storage equipment, while at the same time avoiding the drawbacks of using nitroxyl group-based antipolymerants. In turn, polymer contamination of purified monomer products can be drastically reduced and maintenance costs of said equipment minimized.

In embodiments, the disclosure provides a method for inhibiting the polymerization of monomers in a monomer-containing composition, or a composition that is capable of forming monomer. The method includes a step of adding an aminated quinone antipolymerant to a composition comprising polymerizable monomer, or capable of forming a polymerizable monomer, the antipolymerant being a compound of Formula I or II:

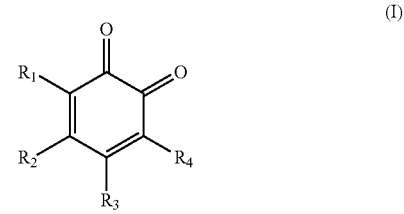

(I)

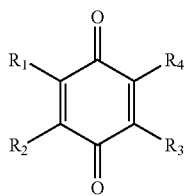

(II)

wherein at least one of —R¹, —R², —R³, and —R⁴, is —NR⁵R⁶, wherein R⁵ and R⁶ are selected from the group consisting of hydrogen, alkyl, aryl, alkyl aryl and aryl alkyl groups of 1 to 24 carbon atoms, with the proviso that both R⁵ and R⁶ are not hydrogen, and any one or more of —R¹, —R², —R³, and —R⁴ that is not —NR⁵R⁶, is selected from the group consisting of hydrogen, alkyl, aryl, alkyl aryl and aryl alkyl, alkoxy, SO₂Ar, COOH, SO₃H, COOR⁹, NHCOR⁹, OCOR⁹ where R⁹ is selected from alkyl, aryl, alkyl aryl and aryl alkyl, or any two adjacent groups of —R¹, —R², —R³, and —R⁴ that are not —NR⁵R⁶ form one or more ring structures. In the method, the aminated quinone of Formula I or II is added without, or with minimal nitroxyl group-containing antipolymerant (less than 50% wt), or is added to a composition comprising polymerizable monomer, or capable of forming a polymerizable monomer, that has no, or very little (less than 50 ppm) nitroxyl group-containing antipolymerant.

In embodiments, any two adjacent groups of —R¹, —R², —R³, and —R⁴ of Formula I or II form an aryl ring structure and provide an aminated quinone antipolymerant according to Formula III or IV:

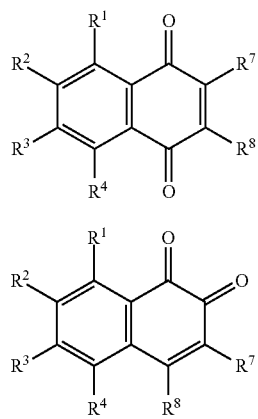

wherein one or both of —R⁷ and/or —R⁸ is or are —NR⁵R⁶, wherein R⁵ and R⁶ are selected from the group consisting of hydrogen, alkyl, aryl, alkyl aryl and aryl alkyl groups of 1 to 24 carbon atoms, with the proviso that both R⁵ and R⁶ are not hydrogen, and any one or more of R¹, R², R³, or R⁴ is or are selected from the group consisting of hydrogen, alkyl, aryl, alkyl aryl and aryl alkyl, alkoxy, SO₂Ar, COOH, SO₃H, COOR⁹, NHCOR⁹, OCOR⁹ where R⁹ is selected from alkyl, aryl, alkyl aryl and aryl alkyl, or two adjacent groups of R¹, R², R³, or R⁴ form one or more ring structures. In the method, the aminated quinone of Formula III or IV is added without, or with minimal nitroxyl group containing antipolymerant as described herein.

In embodiments, the aminated quinone antipolymerant can be provided in a composition for addition to a monomer-containing composition, or a composition that is capable of forming monomer. For example, the composition can include a solvent and solid component consisting essentially of the aminated quinone antipolymerant of Formula I, II, III or IV. Alternatively, the composition can include a solvent and the aminated quinone antipolymerant of Formula I, II, III or IV, with the proviso that the composition includes little or no nitroxyl group-containing antipolymerant.

In embodiments the invention also provides an aminated quinone antipolymerant-containing composition that includes, or that can be added to, one or more polymerizable monomers, or one or more compounds that are capable of forming polymerizable monomers, wherein the composition includes an aminated quinone antipolymerant of Formula I, II, III or IV, with the proviso that the antipolymerant is not 4-anilino-1,2-napthoquinone.

DESCRIPTION OF THE DRAWING

The FIGURE is a graph of the amount of polystyrene polymer formed from styrene monomer solutions in the presence of various aminated quinone antipolymerants of the disclosure (sBANQ, OANQ, and ANQ), and comparative antipolymerants (QMPh, and HTEMPO).

DETAILED DESCRIPTION

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

The disclosure provides methods and compositions that include an aminated quinone antipolymerant to prevent unwanted formation of polymer. The aminated quinone antipolymerant compounds provide excellent antipolymerant activity similar to many nitroxyl group-containing antipolymerants, and therefore do not necessarily require the simultaneous addition of a nitroxyl group-containing antipolymerant for treatment of a monomer stream. In turn, this allows greater flexibility for inhibiting polymerization of a monomer composition, such as when the use of a nitroxyl group-containing antipolymerant is not recommended. Composition and methods of the disclosure are also advantageous in that they can avoid any release of NO$_x$ emissions that would otherwise result from the use of nitroxyl group-containing antipolymerants, and are also non-toxic.

A composition that includes the aminated quinone antipolymerant and any one or more optional component(s) can be in a desired form, such as in a liquid form, a dry form, or as a suspension or dispersion. The aminated quinone antipolymerant can be in a desired physical state in the composition, such as in a dissolved state, in a partially dissolved state, in a suspended state, or in a dry mixture. Also, the aminated quinone antipolymerant can be in a desired form in the composition, such as optionally in a particulate form. If the aminated quinone antipolymerant is in a particulate form, the particles can optionally be described in terms of particle size (e.g., particles of a size range) and/or shape. The form of the composition and the state of the component(s) therein can be chosen by selection of the aminated quinone antipolymerant, with an understanding of its physical properties.

The form of the composition and the state of the component(s) therein can also be affected by the inclusion of one or more optional components, such as a solvent, or solvent mixture, or other excipient compounds like surfactants, dispersants, etc. The form of the composition and the state of the components therein can also be affected by temperature, and composition properties may optionally be described in circumstances at a particular temperature (e.g., at a storage temperature such as 5° C. or below, at room temperature (25° C.), or at a temperature used for monomer synthesis and/or processing (e.g., about 100° C. or greater, about 150° C., about 175° C., etc.).

As noted, an aminated quinone antipolymerant composition can include other components such as a solvent, surfactants, dispersants, etc. If an optional component is present in the composition, it may be described in terms of a weight amount relative to the aminated quinone antipolymerant. The optional component(s) may be present in a weight amount greater than, in an amount about the same as, or an amount less than the aminated quinone antipolymerant.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), greater than about 0.5% (wt), greater than about 0.1% (wt), or greater than about 0.01% (wt), of the total composition. A composition that consists essentially of a solid component that is the aminated quinone antipolymerant (for example, dissolved in a solvent) can optionally include one or more other (e.g., solid) components but in an amount less than about 1% (wt) of the total composition weight. In a composition "consisting of" the recited components there is no other measurable amount of component other than the recited component. In some embodiments, a nitroxyl group-containing antipolymerant can optionally be present in an amount of less than 1% (wt), less than 0.5% (wt), less than 0.1% (wt), or less than 0.01% (wt), of the total composition, and more preferably a nitroxyl group-containing antipolymerant is not present in a detectable level in the composition.

"Antipolymerants" broadly refer to "polymerization inhibitors" and "polymerization retarders" which are compounds that generally inhibit or reduce the formation of polymers from one or more radically polymerizable compounds.

A "polymerization inhibitor," such as nitroxyl group-containing compounds like HTEMPO, in the presence of polymerizable monomers, inhibits the formation of a polymer from those monomers during an induction time. After the induction time has lapsed, the polymer's formation occurs at substantially the same rate as it does in the absence of the polymerization inhibitor.

A "polymerization retarder," which may include an aminated quinone compound as disclosed herein, does not exhibit an induction time, but instead once added to a polymerizable monomer composition reduces the rate at which the formation of the polymer occurs relative to the rate at which it would have formed in the absence of the polymerization retarder.

Polymerization inhibitors, as opposed to polymerization retarders, are generally consumed rapidly. Polymerization retarders, while they slow down the rate of polymerization reactions, are not as effective as polymerization inhibitors. Polymerization retarders, however, are usually not consumed as quickly as polymerization inhibitors.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of non-limiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of", the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

Compositions and methods of the disclosure include or use an antipolymerant that has an aminated quinone chemistry. In embodiments, the aminated quinone antipolymerant includes a partially unsaturated 6 carbon ring structure having at least two, and preferably two, carbonyl groups (—R—C(O)—R—), and at least one, and preferably one, secondary amine group or tertiary amine group (e.g., see $NR^5R^6$ described herein).

In some embodiments the aminated quinone antipolymerant is a compound of Formula I or II:

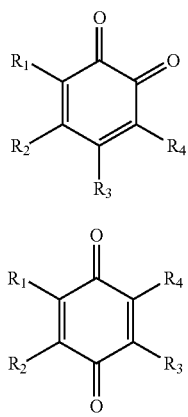

(I)

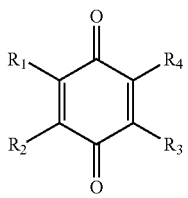

(II)

wherein at least one of —R¹, —R², —R³, and —R⁴ is or are —NR⁵R⁶, wherein R⁵ and R⁶ are selected from the group consisting of hydrogen, alkyl, aryl, alkyl aryl and aryl alkyl groups of 1 to 24 carbon atoms, with the proviso that both R⁵ and R⁶ are not hydrogen, and any one or more of —R¹, —R², —R³, and —R⁴ that is not —NR⁵R⁶, is selected from the group consisting of hydrogen, alkyl, aryl, alkyl aryl and aryl alkyl, alkoxy, SO₂Ar, COOH, SO₃H, COOR⁹, NHCOR⁹, OCOR⁹ where R⁹ is selected from alkyl, aryl, alkyl aryl and aryl alkyl, or any two adjacent groups of —R¹, —R², —R³, and —R⁴ that are not —NR⁵R⁶, form one or more ring structures.

If one or both of R⁵ and R⁶ is or are an alkyl group(s), the alkyl group can be unsaturated, partially saturated, or fully saturated. Fully saturated alkyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, and tetracosyl. Exemplary partially saturated alkyl groups include those based on the saturated alkyl groups as described herein. Partially saturated groups can have one unsaturated group (i.e., a monounsaturated alkyl group), such as exemplified by oleyl or palmitoleyl, or more than one unsaturated group (polyunsaturated, e.g., di-unsaturated, tri-unsaturated, etc.), such as linoleyl, linolenoyl, and arachidonoyl. In preferred embodiments, R⁵ is a partially saturated or fully saturated alkyl group, such as described herein, and R⁶ is hydrogen.

Reflecting the positions of carbonyl groups and amine group(s) on the ring, exemplary aminated quinone antipolymerants can have the general chemistries of 2-amino,1,4-benzoquinone, 2,3-diamino,1,4-benzoquinone, 3,5-diamino,1,4-benzoquinone, 3-amino,1,2-benzoquinone, 4-amino,1,2-benzoquinone, 3,4-diamino,1,2-benzoquinone, 4,5-diamino,1,2-benzoquinone, 3,6-diamino,1,2-benzoquinone, 4,6-diamino,1,2-benzoquinone. The amino group or groups can be any amino group(s) according to the sub-formula —NR⁵R⁶ described herein.

In some embodiments, with reference to Formulas I and II, one of R¹, R², R³, or R⁴ is —NR⁵R⁶, R⁵ is H, and R⁶ is selected from the group consisting of alkyl, aryl, alkyl aryl and aryl alkyl groups of 1 to 24 carbon atoms. Preferably R⁶ is selected from the group consisting of alkyl, aryl, alkyl aryl and aryl alkyl groups of 2 to 22 carbon atoms, and more preferably 3 to 20 carbon atoms. Three of R¹, R², R³, and R⁴ that are not —NR⁵R⁶ are preferably selected from the group consisting of hydrogen, alkyl, aryl, alkyl aryl and aryl alkyl, from the group consisting of hydrogen and C1-C6 alkyl, from the group consisting of hydrogen and C1-C3 alkyl, with preferably, one, two, or three of R¹, R², R³, and R⁴ that are not —NR⁵R⁶ being hydrogen.

Exemplary compounds include 2-alkylamino-1,4-benzoquinones or 2-arylamino-1,4-benzoquinones, such as 2-methylamino-1,4-benzoquinone, 2-ethylamino-1,4-benzoquinone, 2-propylamino-1,4-benzoquinone, 2-butylamino-1,4-benzoquinone, 2-pentylamino-1,4-benzoquinone, 2-hexylamino-1,4-benzoquinone, 2-phenylamino-1,4-benzoquinone, 2-heptylamino-1,4-benzoquinone, 2-octylamino-1,4-benzoquinone, 2-nonylamino-1,4-benzoquinone, 2-decylamino-1,4-benzoquinone, 2-undecylamino-1,4-benzoquinone, 2-dodecylamino-1,4-benzoquinone, 2-tridecylamino-1,4-benzoquinone, 2-tetradecylamino-1,4-benzoquinone, 2-pentadecylamino-1,4-benzoquinone, 2-hexadecylamino-1,4-benzoquinone, 2-heptadecylamino-1,4-benzoquinone, 2-octadecylamino-1,4-benzoquinone, 2-oleylamino-1,4-benzoquinone, 2-nonadecylamino-1,4-benzoquinone, 2-eicosylamino-1,4-benzoquinone, 2-henecosylamino-1,4-benzoquinone, and 2-docosylamino-1,4-benzoquinone, and partially unsaturated alkyl group (e.g., monounsaturated or polyunsaturated) derivatives thereof.

Other exemplary compounds include 2-alkylamino-(3, 5, and/or 6-alkyl)-1,4-benzoquinones or 2-arylamino-(3, 5, and/or 6-alkyl)-1,4-benzoquinones, such as 2-methylamino-(3, 5, and/or 6-methyl)-1,4-benzoquinone, 2-ethylamino-(3, 5, and/or 6-methyl)-1,4-benzoquinone, 2-propylamino-(3, 5, and/or 6-methyl)-1,4-benzoquinone, 2-butylamino-(3, 5, and/or 6-methyl)-1,4-benzoquinone, 2-pentylamino-(3, 5, and/or 6-methyl)-1,4-benzoquinone, 2-hexylamino-(3, 5, and/or 6-methyl)-1,4-benzoquinone, and 2-phenylamino-(3, 5, and/or 6-methyl)-1,4-benzoquinone.

Exemplary compounds include 4-alkylamino-1,2-benzoquinones and 4-arylamino-1,2-benzoquinones, such as 4-methylamino-1,2-benzoquinone, 4-ethylamino-1,2-benzoquinone, 4-propylamino-1,2-benzoquinone, 4-butylamino-1,2-benzoquinone, 4-pentylamino-1,2-benzoquinone, 4-hexylamino-1,2-benzoquinone, 4-phenylamino-1,2-benzoquinone, 4-heptylamino-1,2-benzoquinone, 4-octylamino-1,2-benzoquinone, 4-nonylamino-1,2-benzoquinone, 4-decylamino-1,2-benzoquinone, 4-undecylamino-1,2-benzoquinone, 4-dodecylamino-1,2-benzoquinone, 4-tridecylamino-1,2-benzoquinone, 4-tetradecylamino-1,2-benzoquinone, 4-pentadecylamino-1,2-benzoquinone, 4-hexadecylamino-1,2-benzoquinone, 4-heptadecylamino-1,2-benzoquinone, 4-octadecylamino-1,2-benzoquinone, 4-oleylamino-1,2-benzoquinone, 4-nonadecylamino-1,2-benzoquinone, 4-eicosylamino-1,2-benzoquinone, 4-henecosylamino-1,2-benzoquinone, and 4-docosylamino-1,2-benzoquinone, and partially unsaturated alkyl group (e.g., monounsaturated or polyunsaturated) derivatives thereof.

Other exemplary compounds include 4-alkylamino-(3, 5, and/or 6-alkyl)-1,2-benzoquinones and 4-arylamino-(3, 5, and/or 6-alkyl)-1,2-benzoquinones, such as 4-methylamino-(3, 5, and/or 6-methyl)-1,2-benzoquinone, 4-ethylamino-(3, 5, and/or 6-methyl)-1,2-benzoquinone, 4-propylamino-(3, 5, and/or 6-methyl)-1,2-benzoquinone, 4-butylamino-(3, 5, and/or 6-methyl)-1,2-benzoquinone, 4-pentylamino-(3, 5, and/or 6-methyl)-1,2-benzoquinone, 4-hexylamino-(3, 5, and/or 6-methyl)-1,2-benzoquinone, and 4-phenylamino-(3, 5, and/or 6-methyl)-1,2-benzoquinone.

In some embodiments, with reference to Formulas I and II, two of R¹, R², R³, and R⁴ are —NR⁵R⁶, R⁵ is H, and R⁶ is selected from the group consisting of alkyl, aryl, alkyl aryl and aryl alkyl groups of 1 to 24 carbon atoms. Preferably R⁶ is selected from the group consisting of alkyl, aryl, alkyl aryl and aryl alkyl groups of 2 to 22 carbon atoms, and more preferably 3 to 20 carbon atoms. The two of $R^1$, $R^2$, $R^3$, and $R^4$ that are not —$NR^5R^6$ are preferably selected from the group consisting of hydrogen, alkyl, aryl, alkyl aryl and aryl alkyl, from the group consisting of hydrogen and C1-C6 alkyl, from the group consisting of hydrogen and C1-C3 alkyl, with preferably, one or two of $R^1$, $R^2$, $R^3$, and $R^4$ that are not —$NR^5R^6$ being hydrogen.

Exemplary compounds include 2,5-dialkylamino-1,4-benzoquinones (e.g, 2,5-bis(dialkylamino)-1,4-benzoquinones), 2,3-dialkylamino-1,4-benzoquinones, 3,5-dialkylamino-1,4-benzoquinones, 2-alkylamino-5-arylamino-1,4-benzoquinones, 2-alkylamino-3-arylamino-1,4-benzoquinones, and 3-alkylamino-5-arylamino-1,4-benzoquinones, such as 2,5-bis(dimethylamino)-1,4-benzoquinone, 2,5-bis(diethylamino)-1,4-benzoquinone, 2,5-bis(dipropylamino)-1,4-benzoquinone, 2,5-bis(dibutylamino)-1,4-benzoquinone, 2,5-bis(dipentylamino)-1,4-benzoquinone, 2,5-bis(dihexylamino)-1,4-benzoquinone, 2,5-bis(diphenylamino)-1,4-benzoquinone, 2,3-dimethylamino-1,4-benzoquinone, 2-methylamino-3-ethylamino-1,4-benzoquinone, 2-methylamino-3-hexylamino-1,4-benzoquinone, and 2-methylamino-3-phenylamino-1,4-benzoquinone.

In embodiments, in Formulas I or II, any two adjacent groups of —$R^1$, —$R^2$, —$R^3$, and —$R^4$ form one or more ring structures and provide aminated quinone antipolymerant according to Formula III or IV:

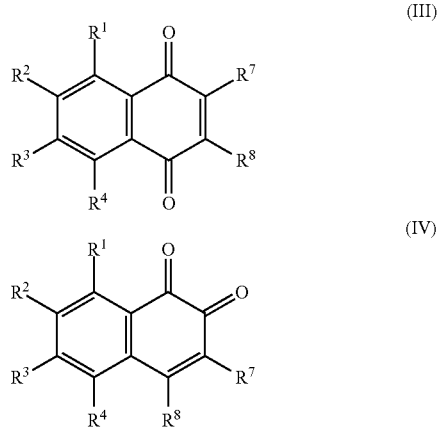

(III)

(IV)

wherein one or both of —$R^7$ and/or —$R^8$ is or are —$NR^5R^6$. In —$NR^5R^6$, $R^5$ and $R^6$ are selected from the group consisting of hydrogen, alkyl, aryl, alkyl aryl and aryl alkyl groups of 1 to 24 carbon atoms, with the proviso that both $R^5$ and $R^6$ are not hydrogen. Further, any one or more of $R^1$, $R^2$, $R^3$, or $R^4$ is or are selected from the group consisting of hydrogen, alkyl, aryl, alkyl aryl and aryl alkyl, alkoxy, $SO_2Ar$, COOH, $SO_3H$, $COOR^9$, $NHCOR^9$, $OCOR^9$ where $R^9$ is selected from alkyl, aryl, alkyl aryl and aryl alkyl. Alternatively, two adjacent groups of $R^1$, $R^2$, $R^3$, or $R^4$ (i.e., $R^1$ and $R^2$; $R^2$ and $R^3$; or $R^3$ and $R^4$) form one or more ring structures. In the method, the aminated quinone of Formula III or IV is added without, or with minimal nitroxyl group containing antipolymerant as described herein.

Exemplary aminated naphthoquinone antipolymerants can have the general chemistries of 2-amino,1,4-naphthoquinone, 2,3-diamino,1,4-naphthoquinone, 2-amino,1,3-naphthoquinone, 4-amino,1,3-naphthoquinone, 2,4-diamino,1,3-naphthoquinone, 3-amino,1,2-naphthoquinone, 4-amino,1,2-naphthoquinone, and 3,4-diamino,1,3-naphthoquinone.

The amino group(s) of Formulas III or IV can be any amino group(s) according to the sub-formula —$NR^5R^6$ described herein. As discussed herein, if one or both of $R^5$ and $R^6$ is or are an alkyl group(s), the alkyl group can be unsaturated, partially saturated, or fully saturated. In preferred embodiments, $R^5$ is a partially saturated or fully saturated alkyl group, such as described herein, and $R^6$ is hydrogen.

In some embodiments of Formula III or IV, either $R^7$ or $R^8$ is —$NR^5R^6$, and $R^6$ is selected from the group consisting of alkyl, aryl, alkyl aryl and aryl alkyl groups of 1 to 24 carbon atoms, and $R^4$ is H. Preferably $R^6$ is selected from the group consisting of alkyl, aryl, alkyl aryl and aryl alkyl groups of 2 to 22 carbon atoms, and more preferably 3 to 20 carbon atoms. Preferably $R^1$, $R^2$, $R^3$, and $R^4$ are selected from the group consisting of hydrogen, alkyl, aryl, alkyl aryl and aryl alkyl, and more preferably hydrogen, C1-6 alkyl, or C1-3 alkyl.

Exemplary compounds of Formula III and IV include 2-alkylamino-1,4-naphthoquinones and 2-arylamino-1,4-naphthoquinones, such as 2-methylamino-1,4-naphthoquinone, 2-ethylamino-1,4-naphthoquinone, 2-propylamino-1,4-naphthoquinone, 2-butylamino-1,4-naphthoquinone, 2-pentylamino-1,4-naphthoquinone, 2-hexylamino-1,4-naphthoquinone, 2-phenylamino-1,4-naphthoquinone (2-anilino-1,4-naphthoquinone), 2-heptylamino-1,4-naphthoquinone, 2-octylamino-1,4-naphthoquinone, 2-nonylamino-1,4-naphthoquinone, 2-decylamino-1,4-naphthoquinone, 2-undecylamino-1,4-naphthoquinone, 2-dodecylamino-1,4-naphthoquinone, 2-tridecylamino-1,4-naphthoquinone, 2-tetradecylamino-1,4-naphthoquinone, 2-pentadecylamino-1,4-naphthoquinone, 2-hexadecylamino-1,4-naphthoquinone, 2-heptadecylamino-1,4-naphthoquinone, 2-octadecylamino-1,4-naphthoquinone, 2-oleylamino-1,4-naphthoquinone, 2-nonadecylamino-1,4-naphthoquinone, 2-eicosylamino-1,4-naphthoquinone, 2-henecosylamino-1,4-naphthoquinone, and 2-docosylamino-1,4-naphthoquinone, and partially unsaturated alkyl group (e.g., monounsaturated or polyunsaturated) derivatives thereof.

Other exemplary compounds include 2-alkylamino-1,3-naphthoquinone or 2-arylamino-1,3-naphthoquinone, such as 2-methylamino-1,3-naphthoquinone, 2-ethylamino-1,3-naphthoquinone, 2-propylamino-1,3-naphthoquinone, 2-butylamino-1,3-naphthoquinone, 2-pentylamino-1,3-naphthoquinone, 2-hexylamino-1,3-naphthoquinone, and 2-phenylamino-1,3-naphthoquinone (2-anilino-1,3-naphthoquinone).

Other exemplary compounds include 2-alkylamino-(5, 6, 7, and/or 8-alkyl)-1,4-naphthoquinones and 2-arylamino-(5, 6, 7, and/or 8-alkyl)-1,4-naphthoquinones, such as 2-methylamino-(5, 6, 7, and/or 8-methyl)-1,4-naphthoquinone, 2-ethylamino-(5, 6, 7, and/or 8-methyl)-1,4-naphthoquinone, 2-propylamino-(5, 6, 7, and/or 8-methyl)-1,4-naphthoquinone, 2-butylamino-(5, 6, 7, and/or 8-methyl)-1,4-naphthoquinone, 2-pentylamino-(5, 6, 7, and/or 8-methyl)-1,4-naphthoquinone, 2-hexylamino-(5, 6, 7, and/or 8-methyl)-1,4-naphthoquinone, and 2-phenylamino-(5, 6, 7, and/or 8-methyl)-1,4-benzoquinone.

Other exemplary compounds include 2-alkylamino-(5, 6, 7, and/or 8-alkyl)-1,3-naphthoquinones and 2-arylamino-(5, 6, 7, and/or 8-alkyl)-1,3-naphthoquinones, such as 2-methylamino-(5, 6, 7, and/or 8-methyl)-1,3-naphthoquinone, 2-ethylamino-(5, 6, 7, and/or 8-methyl)-1,3-naphthoquinone, 2-propylamino-(5, 6, 7, and/or 8-methyl)-1,3-naphthoquinone, 2-butylamino-(5, 6, 7, and/or 8-methyl)-1,3-naphthoquinone, 2-pentylamino-(5, 6, 7, and/or 8-methyl)-1,3-naphthoquinone, 2-hexylamino-(5, 6, 7, and/or 8-methyl)-1,3-naphthoquinone, and 2-phenylamino-(5, 6, 7, and/or 8-methyl)-1,3-benzoquinone.

In some embodiments the disclosure provides an aminated quinone antipolymerant-containing composition that includes, or that can be added to, one or more polymerizable monomers, or one or more compounds that are capable of forming polymerizable monomers, wherein the composition includes an aminated quinone antipolymerant of Formula I, II, III or IV, with the proviso that the antipolymerant is not 4-anilino-1,2-napthoquinone.

Aminated quinone compounds can be prepared from any one or more methods as known in the art. For example, U.S. Pat. No. 3,114,755, discloses the synthesis of mono-substituted aminonaphthoquinones such as 2-methylamino-1,4-naphthoquinone, 2-ethylamino-1,4-naphthoquinone, 2-n-propylamino-1,4-naphthoquinone, 2-isopropylamino-1,4-naphthoquinone, 2-n-butylamino1,4-naphthoquinone, 2-sec-butylamino1,4-naphthoqitinone, 2-Allylamino-1,4-naphthoquinone, 2,5-bis(ethylamino)-1,4-benzoquinone, 2,5-bis(sec-butylamino)-1,4-benzoquinone, by reacting 1,4-benzooquinone or 1,4-naphthoquinone with soluble complex of a copper salt and a primary amine. U.S. Pat. No. 3,379,739 teaches the production of 2,5-diarylamino-1,4-benzoquinone compounds. The synthesis of 2,5-diamino-1,4-benzoquinone is described by in an article published in Mereyala et al. (*Synthesis* (No. 2), 0187-0189, 2007). The synthesis of aminated benzoquinones and aminated naphthoquinones is described by MacGregor et al. (*European Journal of Medicinal Chemistry* 85, 191-206, 2014).

An amount of the aminated quinone antipolymerant, and any other (optional) component in a composition can be described in various ways, such as by a weight percentage (% wt.) or by molar amount of aminated quinone antipolymerant in the composition. When other components are used along with the aminated quinone antipolymerant, such compounds can also be described in terms of weight ratios, or in terms of relative amounts to one another, in a composition.

As discussed herein, an aminated quinone of any of Formulas I, II, III, or IV can be used without, or with minimal nitroxyl group-containing antipolymerant. If a nitroxyl group-containing antipolymerant is included, it can be present in very small amounts, such as in a composition comprising polymerizable monomer, wherein the nitroxyl group containing antipolymerant is not present at all, or present in a very small amount (less than 50 ppm).

For example, in a composition comprising polymerizable monomer and the aminated quinone antipolymerant, a nitroxyl group-containing antipolymerant can optionally be present in an amount of less than 50 ppm, less than 25 ppm, less than 10 ppm, less than 5 ppm, less than 2.5 ppm, less than 2 ppm, less than 1.5 ppm, less than 1 ppm, less than 0.75 ppm, or less than 0.5 ppm.

Nitroxyl group-containing compounds trap propagating monomer radicals in thermally unstable species and inhibit polymerization. A nitroxyl/nitroxide group, which can also be referred to as an amine-N-oxide group, is a functional group including an NO bond and side groups attaching to the nitrogen. Nitroxide (nitroxyl) radicals are oxygen-centered radicals with the free electron delocalized over the N—O bond. Nitroxide-containing polymerization inhibitors can include N—O resonance structures that contributes to the stability of nitroxide radicals.

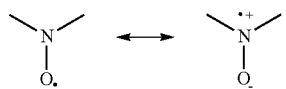

Exemplary nitroxyl/nitroxide-containing compounds which are excluded from compositions from the disclosure, or are used in limited amounts, include, but are not limited to: 2,2,6,6-tetramethylpiperidinyl-1-oxyl (TEMPO), 4-hydroxy-2,2,6,6-tetramethylpiperidinyl-1-oxyl(HTMPO), 4-oxo-2,2,6,6-tetramethylpiperidinyl-1-oxyl (OTEMPO), di-tert-butyl nitroxyl, 1-oxyl-2,2,6,6-tetramethyl-4-n-propoxypiperidine, 1-oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)piperidine, 1-oxyl-2,2,6,6-tetramethylpiperidin-4-yl stearate, 1-oxyl-2,2,6,6-tetramethylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yllaurate, 1-oxyl-2,2,6,6-tetramethylpiperidin-4-yl benzoate, 1-oxyl-2,2,6,6-tetramethylpiperidin-4-yl 4-tert-butylbenzoate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N-(1-oxyl-2,2,6,6-tetramethylpiperidin-4-yl)-caprolactam, N-(1-oxyl-2,2,6,6-tetramethylpiperidin-4-yl)-dodecylsuccinimide, 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, and mixtures thereof. See, for example, U.S. Pat. No. 9,266,797. Any of these compounds can be present at very low amounts (less than 50 ppm, 25 ppm, 10 ppm, etc., as described herein) in a polymerizable monomer composition, or can be excluded from the composition altogether.

Other exemplary nitroxyl/nitroxide-containing compounds include two or three nitroxyl groups. Such compounds may be bis- or tris-compounds. Exemplary bis-nitroxide and tris-nitroxide polymerization inhibitor compound include bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, 2,4,6-tris-[N-butyl-N-(1-oxyl-2,266-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), and mixtures thereof. See, for example, U.S. Pat. No. 9,266,797. Any of these compounds can be present at very low amounts (less than 50 ppm, 25 ppm, 10 ppm, etc., as described herein) in a polymerizable monomer composition, or can be excluded from the composition altogether.

The aminated quinone antipolymerant can be present in a composition with a solvent, or a combination of solvents. A solvent or solvent combination can be chosen so that one or more of the aminated quinone antipolymerant is soluble in the solvent or solvent combination. If the aminated quinone antipolymerant is a liquid at ambient conditions, a miscible solvent can be chosen.

Useful solvents include any solvent in which the aminated quinone antipolymerant is soluble or can be stably suspended. In some embodiments, a solvent or solvent combination can be selected from water soluble or water miscible solvents such glycol-based solvents and hydrophobic or hydrocarbon solvents such as aromatic solvents, paraffinic solvents, or mixtures of both.

Exemplary glycol solvents include, but are not limited to, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as butyl carbitol and butyl CELLOSOLVE™, which contains primarily butyl CARBITOL™, which consists primarily of ethylene glycol monobutyl ether may be used and are available from DOW.

Other exemplary hydrophobic or hydrocarbon solvents include heavy aromatic naphtha, toluene, ethylbenzene, isomeric hexanes, benzene, xylene, such as ortho-xylene, para-xylene, or meta-xylene, and mixtures of two or more thereof.

In some embodiments, the solvent is selected from glycol and aromatic naphtha and combinations thereof.

The amount of aminated quinone antipolymerant (with one or more optional components), in a solvent, or a combination of solvents, can be described one or more ways, such as by the percent solids (wt) of the component(s) in the composition, or by the molar amount of solid components in the composition.

As an example, a stock composition of aminated quinone antipolymerant can be dissolved in a solvent to a concentration of about at least about 0.00001% (wt), at least about 5% (wt), such as in an amount in the range from about 0.00001% (wt) to about 50% (wt).

An amount of the stock composition including aminated quinone antipolymerant can be added to a monomer-containing composition or a composition capable of forming monomer, to provide the antipolymerant at a concentration effective to inhibit polymerization of monomer.

The polymerizable monomer that is subjected to polymerization inhibition by the aminated quinone can include a vinyl or ethylenically unsaturated group. For example, the components of the aminated quinone antipolymerant and any optional component can be added to a composition that includes one or more of the following polymerizable monomers: acrolein, acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyl acetate, vinyltoluene, and vinylpyridine.

The polymerizable monomer can be present in a crude mixture of compounds, a semi-refined mixture of compounds, or a fully-refined mixture of compounds. For example, the aminated quinone antipolymerant can be added to a process stream that includes the polymerizable monomer and one or more other components that are different than the polymerizable monomer. In methods, the aminated quinone antipolymerant can be added before, during, or after, (or combinations thereof) a processing step, such as distillation, wherein compounds in the composition are separated from one another. The aminated quinone antipolymerant can inhibit polymerization of monomer at any one or more stages in a processing system, and therefore reduce or prevent fouling of equipment.

Alternatively, the aminated quinone antipolymerant can be added to a process stream that includes a compound capable of forming into a polymerizable monomer (e.g., a monomer precursor), such as ethylbenzene which is a precursor to styrene. For example, in embodiments, a composition may include a compound that is capable of forming a polymerizable monomer as an unwanted by-product. In this situation, the presence of the aminated quinone antipolymerant can inhibit polymerization of the monomer if it does form as a by-product, and can therefore reduce or prevent fouling of equipment.

In modes of practice, the aminated quinone antipolymerant is introduced into a monomer-containing composition or a composition that includes a compound capable of forming a polymerizable monomer, at a desired concentration effective to inhibit monomer polymerization. The aminated quinone antipolymerant can be added to a composition that includes one or more polymerizable monomers, or one or more compounds that are capable of forming polymerizable monomers. The monomer(s) and/or monomer-forming compound(s) can be present at any concentration in the composition, such as in very small amounts (ppm) or amounts wherein the monomer(s) and/or monomer-forming compound(s) are present in bulk amounts in the composition (e.g., 50% (wt) or greater). Exemplary ranges are from any one of about 5 ppm, about 20 ppm, about 50 ppm, or about 100 ppm (0.1%) to, any one of about 10% (wt), about 25% (wt), about 50% (wt), or about 75% (wt). In some modes of practice, a polymerizable monomer concentration in the range of about 50 ppm to about 200 ppm is used.

The amount of aminated quinone antipolymerant in a composition that includes monomer(s) and/or monomer-forming compound(s) can be chosen based on the monomer/compound type, the amount of monomer/compound in the composition, the type of composition having the monomer/compound, any processing, treatment, or storage conditions for the composition, and the presence of any one or more optional compounds that are different than the aminated quinone antipolymerant and that are added to the composition. The aminated quinone antipolymerant can be added to the composition in an amount to provide a desired level of polymerization inhibition.

In embodiments, the aminated quinone antipolymerant can be used in an amount of at least about 0.10 ppm, such as in the range of about 0.10 ppm to about 50,000 ppm, in the range of about 0.10 ppm to about 25,000 ppm, about 0.10 ppm to about 10,000 ppm, about 25 ppm to about 5,000 ppm, about 25 ppm to about 2,500 ppm, about 50 ppm to about 1,000 ppm, about 50 ppm to about 1,000 ppm, about 75 to about 500 ppm, about 100 to about 300 ppm, about 125 to about 275 ppm, or about 150 to about 250 ppm.

In some modes of practice the aminated quinone antipolymerant is used before or after a polymerizable monomer-containing composition is treated with a polymerization inhibitor that is different than the aminated quinone, such as a nitroxide group-containing polymerization inhibitor (e.g., HTEMPO, etc.). In some modes of practice, the aminated quinone antipolymerant is added to a polymerizable monomer composition after the composition has been treated with a nitroxide-containing polymerization inhibitor, and the inhibitor has been at least substantially consumed or has otherwise at least lost most of its inhibitor activity. For example, a nitroxide group-containing polymerization inhibitor can be added to a monomer-containing composition at a first time point and then the composition can be monitored to determine any increase in the formation of polymer and/or presence of inhibitor, and if there is an increase in formation of polymer or reduction in inhibitor, the aminated quinone antipolymerant can be added at a second time point to maintain inhibition of polymerization.

In other modes of practice, the aminated quinone antipolymerant can be added to a monomer-containing composition at a first time point, and then one or more other compounds useful for inhibiting polymerization that is different than the aminated quinone can be added to the composition at one or more later time point(s) (e.g., second, third, etc.).

The aminated quinone antipolymerant can be added to a polymerizable monomer composition in any one or more different ways, such as addition of the antipolymerant in single dose, continuous addition, semi-continuous addition, intermittent addition, or any combination of these methods. In a continuous addition, the aminated quinone antipolymerant can be added at a constant or variable rate. The mode or modes of addition of the aminated quinone antipolymerant can be chosen based on the polymerizable monomer-containing composition and how it is being stored, processed, or otherwise treated. For example, in a process stream involving the movement and separation of polymerizable monomer, or a compound that can form a polymerizable monomer, from other components such as a distillation apparatus, the aminated quinone antipolymerant can be added in a continuous or semi-continuous manner to account for new monomer or monomer precursor constantly being introduced.

The term "fouling" refers to the formation of polymers, prepolymers, oligomer and/or other materials which would become insoluble in and/or precipitate from a stream and deposit on equipment under conditions of operating the equipment. In turn, the aminated quinone antipolymerant can be referred to as an "antifoulant" as it prevents or reduces such formation.

Optionally, the ability of the compositions of the disclosure to inhibit polymerization can be described relative to a composition that does not include the aminated quinone antipolymerant, or that includes a comparative compound. The effect of the aminated quinone antipolymerant can be understood by measuring the formation of a polymer (e.g., polystyrene) in a monomer (e.g., styrene) composition over time, in the presence of a composition that includes the aminated quinone antipolymerant as compared to one that does not include the aminated quinone antipolymerant, or that uses an antipolymerant having chemistry that is different than one of the disclosure.

For example, a composition of the disclosure with an aminated quinone antipolymerant can inhibit polymerization of monomer by more than 50%, by more than 60%, by more than 70%, by more than 80%, by more than 85%, by more than 90%, by more than 92.5%, by more than 95%, or by more than 97%, as compared to a composition with a non-aminated quinone (e.g., a di-butyl-1,4-benzoquinone), under the same conditions.

The aminated quinone antipolymerant can be used in conjunction with compositions containing polymerizable monomers and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by monomer polymerization. This term also includes sets of these components where more than one of the components is part of a "system."

In one preferred method of use, a composition of the disclosure with aminated quinone antipolymerant and solvent (e.g., glycol) is used with a process that involves a distillation tower that is used to separate and purify vinylic monomers, such as styrene. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity. Optionally, the aminated quinone antipolymerant is used along with one or more secondary components such as stabilizers like butylated hydroxytoluene (BHT) and tert-butylcatechol (TBC). In an exemplary mode of practice these components are used in a distillation tower that is used to separate and purify vinylic monomers.

The aminated quinone antipolymerant-containing composition can be introduced into a stream leading from the reaction bed to the distillation tower, or can be directly added to the distillation tower. The compositions can be added prior to heating the monomer composition or while heating the monomer composition in the distillation tower. In embodiments, the aminated quinone antipolymerant compound has a boiling point that is higher than that of the desired compound or distillate (e.g., a monomer such as styrene) subject to distillation tower and during the distillation process the desired compound is separated from the aminated quinone antipolymerant compound by virtue of temperature difference. In embodiments, the boiling point difference between the compound of interest and the aminated quinone antipolymerant can be about 10° C. or greater, about 15° C. or greater, about 20° C. or greater, about 25° C. or greater, about 30° C. or greater, about 35° C. or greater, about 40° C. or greater, about 45° C. or greater, or about 50° C. or greater.

Alternatively, or in addition to adding the aminated quinone antipolymerant during a distillation process, the composition can be optionally or further added to a distillation effluent stream, such as a purified styrene stream. Optionally, another antipolymerant can be added to a distillation effluent stream prior to or along with the aminated quinone antipolymerant.

The aminated quinone antipolymerant, optionally used in combination with one or more other components, can be used with any "hydrocarbon process stream" which can include unsaturated monomer in order to stabilize the stream during transportation and storage. In some modes of practice, the aminated quinone antipolymerant can be used in conjunction with a "petroleum product" which refers to any hydrocarbon product obtained from a subterranean reservoir, any product derived therefrom, or any mixture thereof. Polymerizable monomers are found in or can be chemically derived from petroleum products. Nonlimiting examples of petroleum products include but are not limited to crude oil, reduced crude oil, crude distillate, heavy oil, or bitumen, hydrotreated oil, refined oil, byproducts of petroleum product processing such as pyrolysis, hydrotreating, or phase separation, or mixtures of two or more of these. A liquid petroleum product is a petroleum product that is substantially a liquid at 20° C.

The aminated quinone antipolymerant can be added to or can be present in a "petroleum process stream" which refers to any petroleum product disposed within petroleum process equipment in fluid contact with an interior surface thereof.

The petroleum process stream can include, or can be capable of forming as a by-product, one or more polymerizable monomer. The process stream may be substantially static, such as a petroleum product disposed within in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a man-made item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including the aminated quinone antipolymerant are thermally stable and have antipolymerant activity in processing streams or other polymerizable monomer-containing compositions at temperatures of about 20° C. to about 400° C., for example about 100° C. to 400° C., or about 100° C. to 350° C., or about 100° C. to 300° C., or about 100° C. to 250° C., or about 100° C. to 200° C., or about 100° C. to 150° C.

In embodiments, compositions including aminated quinone antipolymerant can be introduced into a composition with a polymerizable monomer, such as a liquid petroleum process stream in a batch-wise, a continuous, or a semi-continuous manner. In some embodiments, the aminated quinone antipolymerant (and any other optional component) are introduced manually; and in other embodiments, their introduction is automated. In embodiments, the amount of the aminated quinone antipolymerant introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the aminated quinone antipolymerant is added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. In embodiments, the antipolymerant is added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein.

Equipment containing the polymerizable monomer-containing compositions that are treated with the aminated quinone antipolymerant and any other optional component can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The aminated quinone antipolymerant can also inhibit unwanted polymerization and fouling of the process equipment in a primary fractionation process, light ends fractionation, non-aromatic halogenated vinyl fractionation and stabilization, process-gas compression, dilution steam system, caustic tower, quench water tower, quench water separator (pyrolysis gasoline), butadiene extraction, propane dehydrogenation, diesel and petrol fuel stabilization, olefin metathesis, styrene purification, hydroxyhydrocarbon purification, stabilization of vinylic monomers during transportation and storage, or delays the polymerization of resins and compositions comprising ethylenically unsaturated species.

The aminated quinone antipolymerant can be added at any given point in a process and at one or more locations. For example, an antipolymerant composition can be added directly at the interstage coolers or compressors or upstream of the inter-coolers or compressors. The aminated quinone antipolymerant can be added continuously or intermittently to the process equipment as required preventing or reducing fouling.

The aminated quinone antipolymerant can be introduced to desired systems by any suitable method. For example it may be added in neat or a dilute solution. In some embodiments, a composition containing the aminated quinone antipolymerant can be applied as a solution, emulsion, or dispersion that is sprayed, dripped, poured or injected into a desired opening within a system or onto the process equipment or process condensate. In some embodiments, the composition may be added with a washoil or an attemperation water.

After introducing the composition to process equipment, treated process equipment can be observed to have less deposition on equipment than in process equipment without addition of the composition. Reduction or prevention in fouling can be evaluated by any known method or test. In some embodiments, the reduction or prevention of fouling can be accessed by measuring the time it takes for a sample with and without the antifoulant composition to gel.

Example 1: Synthesis of AminoNaphthoquinones

A prototype of amino-naphthoquinone architectures, 2-anilino-1,4-napthoquinone, was synthesized according to the method detailed in the *European Journal of Medicinal Chemistry* 85, 191-206 (2014). Into a 1L, three-necked armed with a condenser and a dropping funnel was charged 24.0 g (147.2 mmoles) of 1,4-naphthoquinone along with a magnetic follower. A copious amount of methanol was charged, with the contents thereafter stirred vigorously into a slurry. Aniline, 13.5 mL (147.2 mmoles), diluted with methanol was added to the dropping funnel from which the solution was added dropwise into the flask. On completion of the reaction, the solvent was removed in vacuo. The purity of the target compound was confirmed using gas chromatography. Analyses using H-NMR and $^{13}$C-NMR confirmed the structure of 2-anilino-1,4-napthoquinone.

Example 2. Synthesis of 2-sec-Butylaminonaphthoquinone

The method in Example 1 was used to synthesize, isolate and analyze the other aminated naphthoquinones tested as prototypes.

Example 3. Synthesis of 2-Oleylaminonaphthoquinone

2-Oleylaminonaphthoquinone was synthesized, recovered and characterized using the method in Example 1.

Example 4: Performance of 2-Anilino-1,4-Napthoquinone in Styrene

A styrene solution, 300 g, comprising 200 ppm 2-anilino-1,4-napthoquinone was prepared. The 4-tert-butylcatechol (TBC) stabilizer in the commercial styrene had been removed just before the treatment composition. Using an alumina column, said stabilizer was removed. For the polymerizations reactions, twenty-four Ace Glass #15 threaded pressure tubes equipped with PTFE screw caps and fluoroelastomer (FETFE) O-rings were used are the polymerization reactors. Into each tube were charged 10 mL of the reaction solution. Dissolved oxygen in each solution in the tubes was purged by sparging with nitrogen for 2 minutes, with each tube immediately sealed and the solution kept under a nitrogen headspace. The tubes were loaded into a heating block that had been preheated to 120° C. At regular time intervals, four tubes were retrieved from the block and the polymerization reaction quenched by cooling in an ice bath. The cooled polymer solutions were immediately diluted with toluene. A proprietary method was also used to measure the polymer content.

Example 5: Performance of 2-sec-Butylaminonaphthoquinone in Styrene

The method in Example 3 was used to determine the performance of 2-sec-Butyl aminonaphthoquinone.

Example 6: Performance of 2-Oleylaminonaphthoquinone in Styrene

Using the method in Example 3, the performance of 2-Oleylaminonaphthoquinone as an antipolymerant was carried out.

Example 7: HTEMPO in Styrene

Similarly, HTEMPO was dissolved in de-inhibited styrene to give 200 ppm in 300 g of solution. Using the procedure in Example 2, the antipolymerant activity of HTEMPO was determined.

Example 4: 7-Phenyl Quinone Methide (7-PhQM) in Styrene

For another comparative purpose, a solution of 200 ppm of 7-PhQM in 300 g of inhibitor-free styrene was prepared after which the antipolymerant performance was tested according to the procedure in Example 1.

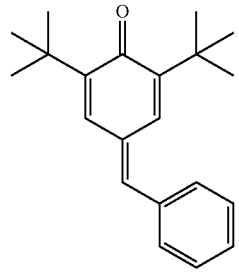 [SMILES: CC(C)(C)C1=CC(=Cc2ccccc2)C=C(C(C)(C)C)C1=O]

Example 6: Untreated Styrene

Immediately after removing TBC from styrene, 10-mL aliquots of said styrene were charged into each of the afore-mentioned pressure tubes. After the dissolved oxygen was purged out of the solutions, polymerizations reactions and polymer analysis were conducted in accordance with the procedure in Example 1.

TABLE 1

Performance of antipolymerants in styrene at 200 ppm.

| Time | Blank | 200 ppm QMPh | 200 ppm HTEMPO | 200 pm (0.87 mmol) sBANQ | 0.87 mmolal OANQ | 200 ppm ANQ |
| --- | --- | --- | --- | --- | --- | --- |
| 30 | 3.89 | 0.199 | 0.0166 | 0.0366 | 0.0561 | 0.0646 |
| 45 | 5.49 | 0.331 | 0.0231 | 0.0444 | 0.0628 | 0.0722 |
| 60 | 7.50 | 0.531 | 0.0301 | 0.0472 | 0.0734 | 0.128 |
| 75 | 9.31 | 0.601 | 0.0343 | 0.0885 | 0.0762 | 0.217 |
| 90 | 12.1 | 0.864 | 0.0654 | 0.156 | 0.0879 | 0.567 |
| 105 | 13.8 | 1.05 | 1.92 | 0.269 | 0.162 | 1.68 |
| 120 | 16.4 | 1.22 | 2.82 | 0.739 | 0.717 | 3.18 | sBANQ: 2-sec-butylaminonaphthoquinone:
OANQ: 2-oleylaminonaphthoqionone:
ANQ: 2-anilinonaphthoquinone

What is claimed is:

1. A method for inhibiting the polymerization of monomers in a monomer-containing composition, the method comprising:
adding an aminated quinone antipolymerant to a composition comprising polymerizable monomer or capable of forming a polymerizable monomer, the antipolymerant being a compound of Formula III or IV:

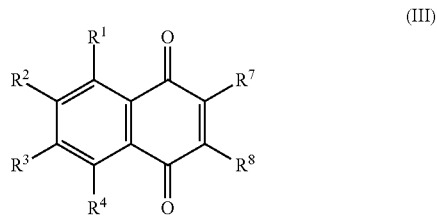

-continued

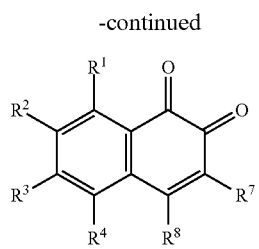

(IV)

wherein one or both of —R⁷ or —R⁸ is —NR⁵R⁶, wherein R⁵ and R⁶ are selected from the group consisting of hydrogen, alkyl, aryl, alkyl aryl and aryl alkyl groups of 1 to 24 carbon atoms, with the proviso that both R⁵ and R⁶ are not hydrogen and at least one of R⁵ and R⁶ is an alkyl group having an amount of carbon atoms in the range of 1-24, and —R¹, —R², —R³, and —R⁴ are selected from the group consisting of hydrogen, alkyl, aryl, alkyl aryl, and aryl alkyl, alkoxy, SO₂Ar, COOH, SO₃H, COOR⁹, NHCOR⁹, OCOR⁹ where R⁹ is selected from alkyl, aryl, alkyl aryl, and aryl alkyl, or any two adjacent groups of —R¹, —R², —R³, and —R⁴ that are not —NR⁵R⁶ form one or more ring structures, and wherein the composition has no, or less than 50 ppm of a nitroxyl group containing antipolymerant.

2. The method of claim 1 wherein —R¹, —R², —R³, and —R⁴ are selected from the group consisting of hydrogen and C1-C6 alkyl.

3. The method of claim 2 wherein three of —R¹, —R², —R³, or —R⁴ that are not —NR⁵R⁶ are hydrogen.

4. The method of claim 1 wherein the alkyl group of R⁶ has 2 to 22 carbon atoms.

5. The method of claim 1, wherein R⁷ is —NR⁵R⁶, R⁸ is H, and R¹, R², R³, and R⁴ are selected from the group consisting of hydrogen, alkyl, aryl, alkyl aryl and aryl alkyl.

6. The method of claim 1 wherein one, two, three, or all of R¹, R², R³, and R⁴ are hydrogen.

7. The method of claim 4 wherein the alkyl group of R⁶ has 3 to 20 carbon atoms.

8. The method of claim 1 wherein the compound of Formula III is selected from the group consisting of 2 ethylamino-1,4-naphthoquinone, 2-propylamino-1,4-naphthoquinone, 2-butylamino-1,4-naphthoquinone, 2-pentylamino-1,4-naphthoquinone, 2-hexylamino-1,4-naphthoquinone, 2-heptylamino-1,4-naphthoquinone, 2-octylamino-1,4-naphthoquinone, 2-nonylamino-1,4-naphthoquinone, 2-decylamino-1,4-naphthoquinone, 2-undecylamino-1,4-naphthoquinone, 2-dodecylamino-1,4-naphthoquinone, 2-tridecylamino-1,4-naphthoquinone, 2-tetradecylamino-1,4-naphthoquinone, 2-pentadecylamino-1,4-naphthoquinone, 2-hexadecylamino-1,4-naphthoquinone, 2-heptadecylamino-1,4-naphthoquinone, 2-octadecylamino-1,4-naphthoquinone, 2-oleylamino-1,4-naphthoquinone, 2-nonadecylamino-1,4-naphthoquinone, 2-eicosylamino-1,4-naphthoquinone, 2-henecosylamino-1,4-naphthoquinone, and 2-docosylamino-1,4-naphthoquinone, and partially unsaturated alkyl group derivatives thereof.

9. The method of claim 1, wherein the aminated quinone antipolymerant is present in the composition in an amount in the range of 10 to 50000 ppm, an amount in the range of 50 to 5000 ppm, or an amount in the range of 100 to 300 ppm.

10. The method of claim 1 wherein the polymerizable monomer comprises a vinyl or ethylenically unsaturated group.

11. The method of claim 10 wherein the polymerizable monomer is selected from the group consisting of acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyltoluene, vinylpyridine, divinylbenzenze, ethylene, acetylene, methylacetylene, vinylacetylene, propylene, butene, butyne, butadiene, cyclopentadiene, dicyclopentadiene, and indene.

12. The method of claim 1 wherein the composition comprises styrene or ethylbenzene.

13. The method of claim 1 wherein the composition includes one or more non-polymerizable hydrocarbons.

14. The method of claim 1 which is performed during purification or processing of one or more components of the composition.

15. The method of claim 1 wherein the composition has less than 5 ppm of a nitroxyl group containing antipolymerant, less than 0.5 ppm of a nitroxyl group containing antipolymerant, or no nitroxyl group containing antipolymerant, wherein the nitroxyl group containing antipolymerant is optionally selected from the group consisting of 2,2,6,6-tetramethylpiperidinyl-1-oxyl (TEMPO), 4-hydroxy-2,2,6,6-tetramethylpiperidinyl-1-oxyl(HTMPO), 4-oxo-2,2,6,6-tetramethylpiperidinyl-1-oxyl(OTEMPO), or a combination thereof.

16. The method of claim 1 wherein the aminated quinone antipolymerant inhibits polymerization of monomer by more than 50%, or more than 90%, as compared to a composition with a non-aminated quinone under the same conditions.

17. The method of claim 1, wherein the polymerizable monomer is present in the composition in the range of about 5 ppm to about 50% (wt), about 20 ppm to about 10% (wt), or about 50 ppm to about 200 ppm.

* * * * *

UNITED STATES PATENT AND TRADEMARK OFFICE
CERTIFICATE OF CORRECTION

| | |
|---|---|
| PATENT NO. | : 11,312,793 B2 |
| APPLICATION NO. | : 16/580653 |
| DATED | : April 26, 2022 |
| INVENTOR(S) | : Jonathan Masere |

It is certified that error appears in the above-identified patent and that said Letters Patent is hereby corrected as shown below:

On the Title Page

Column 2
Item (56) Other Publications, Line 28, Delete "trypanoddal" and insert --trypanocidal--.

Column 2
Item (56) Other Publications, Line 29, Delete "of" and insert --&--.

Column 2
Item (56) Other Publications, Line 29, Delete "Chemisuy," and insert --Chemistry,--.

Column 2
Item (56) Other Publications, Line 34, Delete "4-naphthoquines"," and insert --4-naphthoquinone",--.

In the Claims

Column 21
Claim 8, Line 42, "2" should be --2- --.

Column 22
Claim 8, Line 5, "2-henecosylamino-1," should be --2-heneicosylamino-1,--.

Column 22
Claim 11, Lines 21-22, "divinylbenzenze," should be --divinylbenzene,--.

Signed and Sealed this
Sixteenth Day of May, 2023

Katherine Kelly Vidal
*Director of the United States Patent and Trademark Office*